United States Patent [19]
Garry, Jr. et al.

[11] Patent Number: 5,364,757
[45] Date of Patent: Nov. 15, 1994

[54] METHODS OF SUPPORTING A DIAGNOSIS OF SYSTEMIC LUPUS ERYTHEMATOSUS

[75] Inventors: Robert F. Garry, Jr., New Orleans; Cesar D. Fermin, Mandeville, both of La.; Steve S. Alexander, Jr., Gaithersburg, Md.

[73] Assignee: Administrators of the Tulane Educational Fund, New Orleans, La.

[21] Appl. No.: 805,437

[22] Filed: Dec. 11, 1991

Related U.S. Application Data

[63] Continuation-in-part of Ser. No. 526,349, May 21, 1990, abandoned.

[51] Int. Cl.$^5$ .......................... C12Q 1/70; C12Q 1/00; G01N 33/564; G01N 33/53
[52] U.S. Cl. .......................................... 435/5; 435/4; 435/7.1; 435/235.1; 435/239; 930/221
[58] Field of Search ..................... 435/7.1, 235.1, 239, 435/236, 5, 4

[56] References Cited

PUBLICATIONS

Garry et al., 1990, Science 250:1127–1129.
Talal et al., 1990, Faseb J. 4:(7)A2102, Abstract No. 2369.
Talal et al., 1990, Arthritis and Rheumatism 33:774–781.
Etkin et al., 1989, Acta Virol. 33:151–161.
Kam-Hansen et al., 1989, Acta Neurol. Scand. 80:467–471.
Ascher et al., 1988, Clin. Exp. Immunol. 73:165–167.
Rucheton et al., 1987, Biol. of the Cell 60:71–72.
Query et al., 1987, Cell 51:211–220.
Leiter et al., 1986, J. Exp. Med. 163:87–100.
Ziegler et al., 1986, Clin. Immunol. Immunopath. 41:305–313.
Ono et al., 1986, in Abstracts of 14th International Cancer Congress, Budapest, Hungary Aug. 12–27, vol. 2, p. 626, Abstract No. 2394.
Maeda et al., 1985, Clin. Exp. Immunol. 60:645–653.
Ono et al., 1985, Keio J. Med. 34:1–16.
Rucheton et al., 1985, Virology 144:468–480.
Barré-Sinoussi et al., 1983, Science 220:868–871.
Belkin et al., 1982, J.Rheumatol 9:613–616.
Datta et al., 1982, J. Immunol. 129(4):1539–1544.
Kelley et al., 1981, Clin. Immunol. Immunopath. 21:190–203.
Suni et al., 1981, Int. J. Cancer 28:559–566.
Hart et al., 1979, Annals of the Rheumatic Diseases 38:514–525.
Lueders et al., 1979, J. Virol. 30:225–231.
Datta et al., 1978, J. Exp. Med. 147:854–871.
Datta et al., 1978, J. Exp. Med. 147:872–881.
Oldstone et al., 1976, J. Virology 18(1):176–181.
Talal et al., 1974, Curr. Topics Microbiol. Immunol. 64:79–103.
Yang and Wivel, 1973, J. Virol. 11(2):287–298.
The Merck Index, 11th ed., 1989, p. 490, entry 3092.
The Merck Index, 11th ed., 1989, p. 1597, entry 10023.

*Primary Examiner*—Jacqueline Stone
*Assistant Examiner*—Johnny F. Railey, II
*Attorney, Agent, or Firm*—Pennie & Edmonds

[57] ABSTRACT

The present invention relates to the discovery of a novel retroviral particle associated with autoimmune disease. New methods of diagnosis and treatment of autoimmune disease, novel cell lines comprising the new retrovirus, assay systems that may be used in the development of antiretroviral pharmaceuticals, and model systems for the study of autoimmune diseases and acquired immunodeficiency syndrome (AIDS) are provided by the present invention.

3 Claims, 4 Drawing Sheets

METHODS OF SUPPORTING A DIAGNOSIS OF SYSTEMIC LUPUS ERYTHEMATOSUS

This application is a continuation-in-part of U.S. Pat. application No. 07/526,349 filed May 21, 1990 now abandoned.

TABLE OF CONTENTS

1. Introduction
2. Background Of The Invention
   2.1. The Role Of Retroviruses In Autoimmune Disease
   2.2. Similarities Between Human Immunodeficiency Virus Infection And Autoimmune Disease
3. Summary Of The Invention
4. Description Of The Figures
5. Detailed Description Of The Invention
   5.1. Methods Of Culturing And Isolating The Autoimmune Disease-Associated Retrovirus
   5.2. Methods Of Diagnosis
   5.3. Methods Of Treatment
   5.4. Model Systems For The Study of Disease
   5.5. Assay Systems of the Invention
6. Example: Sjogren's Syndrome: Initial Characterization Of A HIV-Related Intracisternal A-Type Retroviral Particle Present In Lymphoblastoid Cells Exposed To Salivary Gland Homogenates
7. Example: Detection Of Antibodies Directed Toward HIV And HIV-Related Intracisternal A-Type Retroviral Particle In Patients With Various Autoimmune Diseases
   7.1. Materials and Methods
   7.1.1. Western Blotting
   7.1.2. ELISA
   7.2. Results
   7.2.1. Reactivity Of Autoimmune Disease Patient Sera With HIV Proteins
   7.2.2. Reactivity Of Autoimmune Disease Patient Sera With HIAP Proteins
   7.2.3. ELISA Assays

1. INTRODUCTION

The present invention relates to the discovery of a novel retroviral particle associated with a number of human diseases, in particular, diseases categorized as autoimmune diseases. New therapeutic and diagnostic methods, novel cell lines comprising the new retrovirus, assay systems that may be used in the development of antiretroviral pharmaceuticals, and model systems for the study of diseases are provided by the present invention.

2. BACKGROUND OF THE INVENTION

2.1. THE ROLE OF RETROVIRUSES IN AUTOIMMUNE DISEASE

Retroviral etiology for several human autoimmune diseases has been proposed, and is the subject of some controversy (Pincus, 982, Arthritus Rheum. 25: 847–856; Norval, 1979, Annals of the Rheumatic Diseases 3:8:507–513; Hart et al., 1979, Annals of the Rheumatic Diseases 38:514–525; Deman et al., 1976, Transplantation Reviews 31:79–115; Talal, 1978, in "Autoimmunity: Genetic, Immunologic, Virologic and Clinical Aspects," Academic Press, London). It has been demonstrated that self-reactive antibodies in autoimmune diseases, called autoantibodies, may react with components of retroviruses. For example, Rucheton et al. (1987, Biology of the Cell 60:71–72) reports that human autoantibodies reactive with HnRNP, a human ribonucleoprotein molecule also react with the p30 gag protein of a mouse retrovirus.

Often experiments linking retroviruses with particular autoimmune diseases have failed to produce consistent results. For example, Phillips et al. (1978, Annals of the Rheumatic Diseases 35:422–428) reported isolating a retrovirus from the placenta of a systemic lupus erythematosus (SLE) patient, after previously being unable to do so (Phillips et al., 1976, Annals of the Rheumatic Diseases 35:422–428). Further, particles resembling retroviruses have been observed in placentas of SLE patients at a higher frequency than normal placentas (Imamura et al., 1976, Am. J. Pathol. 83:3:383–394) but interestingly, have not been observed in organs typically involved by SLE (e.g. spleen and kidney).

The literature indicates that a number of researchers are exploring the role of retroviruses in autoimmune disease. For example, Ono et al. (1985, Keio Journal of Medicine 34:1–16), reasoning that the thymus gland is frequently involved in autoimmune disease, cultured thymus cells of autoimmune patients (mainly afflicted with myasthenia gravis, ulcerative colitis, or pure red cell aplasia) with B cells and observed the appearance of retrovirus particles in the cultured thymus cells. Suni et al. (1981, Int. J. Cancer 28:559–566) observed that an antigen related to a retroviral p30 antigen was expressed in highly differentiated syncytiotrophoblasts in human placenta, and suggested that retrovirus-reactive antibodies may represent an autoimmune-like immune response to p30 related antigen which may have escaped during cellular damage (see also Maeda, 1985, Clin. Exp. Immunol. 60:645–653). Kam-Hansen et al. (1989, Acta Neurol. Scand. 80:467–471) has suggested a role for retroviruses in multiple sclerosis. Leiter et al. (1986, J. Exp. Med. 163:87–100) describes a mouse animal model system for diabetes and suggests that retroviral proteins, normally sequestered within pancreatic beta cells, may be expressed on the cell surface as a result of high serum glucose, resulting in autoimmune elimination of glucose-stressed beta cells.

Interestingly, AIDS has been hypothesized to be, at least in part, an autoimmune disease directed at the immune system and triggered by a lymphotrophic retrovirus (Ziegler and Stites, 1986, Clin. Immunol. Immunopathol. 41:305–313). Ziegler and Stites (ibid) have suggested that HIV antigens expressed on the lymphocyte surface may mimic MHC antigens, provoking an autoimmune attack on MHC-bearing cells. Ascher and Sheppard (1988, Clin. Exp. Immunol. 73:165–167) propose that latency of AIDS is not due to delayed viral expression and growth but rather to the accumulation of insults to an immune system with abnormal regulatory mechanisms induced by HIV infection of macrophages.

2.2. SIMILARITIES BETWEEN HUMAN IMMUNODEFICIENCY VIRUS INFECTION AND AUTOIMMUNE DISEASE

Several autoimmune diseases share clinical characteristics with disease induced by human immunodeficiency virus (HIV) (Morris et al., 1982, Ann. Intern. Med. 96:714–717; Walsh et al., 1984, New Eng. J. Med. 311:635–639; Stricker et al., 1985, New Eng. J. Med. 313:1375–1380; Dalakas et al., 1986, J.A.M.A.

256:2381–2383; Duvic et al., 1987, J. Am. Acad. Dematol. 17:656–662; Winchester et al., 1987, Ann. Inter. Med. 106:19–26; deClerk et al., 1988, Arthritis and Rheumatism 31:272–275; Berman et al., 1988, Am. J. Med. 85:59–64; Calabrese et al., 1989, Arthritis and Rheumatism 32:1453–1457; Kopelman and Zolla-Pazner, 1988, Am. J. Med. 84 (1):82–88; Rynes et al., 1988, Am. J. Med. 84:810–816; Itescu et al., 1989, Lancet pp. 466–468; Schiot et al., 1989, AIDS 3:819–822 ). Patients infected with HIV often manifest fever, lymphadenopathy, rash, renal dysfunction, neurologic abnormalities, weight loss, leukopenia, anemia, and hypergammaglobulinemia (Kopelman and Zolla-Pazner, 1988, Am. J. Med. 84:82–88; Masur et al., 1981, N. Engl. J. Med. 305:1431–1438; Spivak et al., 1984, Am. J. Med. 77:224–228). These symptoms and signs are often exhibited by patients suffering from autoimmune diseases.

Several researchers have studied conditions in which the clinical syndromes of HIV infection and autoimmunity are similar. Kopelman and Zolla-Pazner (supra) studied five patients ultimately diagnosed as having AIDS or AIDS-related complex in whom the differential diagnosis included systemic lupus erythematosus (SLE) because of multisystem disease and autoimmune phenomena (including antinuclear antibodies). Their observations led them to suggest that SLE and HIV share clinical and serologic features. Rynes et al. (1988, Am. J. Med. 84:810–816) describe an AIDS-associated arthritis. Winchester et al. (1987, Ann. Int. Med. 106:19–26) report thirteen patients who had co-occurrence of severe Reiter's Syndrome (an asymmetric oligoarthritis) and AIDS or AIDS-related syndrome.

Primary Sjogren's Syndrome (SS) is principally characterized by dryness of the mouth and eyes (sicca syndrome) which is also a common manifestation of HIV infection (deClerk et al., 1988, Arthritis and Rheumatism 31:272–275; Calabrese et al., 1989, Arthritis and Rheumatism 32:1453–1457; Itescu et al., 1989, Lancet pp. 466–468; Schiot et al., 1989, AIDS 3:819–822). The dryness in both SS and HIV infection is due to destruction of the salivary and lacrimal glands which is accompanied by lymphocytic infiltration. The lymphocytes of approximately 70% of SS patients eventually also infiltrate lung, kidney and muscle as the disease progresses. As in HIV disease, localized or generalized lymphadenopathy may develop. In 5–10% of primary SS patients, there is a severe weight loss which is reminiscent of HIV-induced wasting. SS patients also produce a variety of autoantibodies, as do persons with other autoimmune diseases and AIDS.

3. SUMMARY OF THE INVENTION

The present invention relates to purified preparations of a novel retrovirus, diagnostic and therapeutic methods, novel cell lines, and assay and model systems for the study of various diseases. It is based, at least in part, on the discovery of a novel retrovirus which is antigenically similar to human immunodeficiency virus but which appears to comprise a functionally distinct reverse transcriptase.

According to the present invention, various diseases, including diseases traditionally classified as autoimmune diseases, such as Sjogren's Syndrome, Scleroderma, Systemic Lupus Erythematosus, and Juvenile Rheumatoid Arthritis, may be diagnosed, and their clinical course may be monitored, by demonstrating the presence of anti-retroviral antibodies and/or measuring the levels of such antibodies. In preferred embodiments of the invention, antibodies that recognize a 45,000 dalton, 61,000 dalton, and/or 70,000 dalton protein of the retrovirus of the invention are detected and/or measured. Alternatively, diseases may be diagnosed or monitored by detecting the presence of antibodies directed toward particular retroviral peptides, such as, for example, peptide K, or by directly or indirectly demonstrating viral particles in the cells of a patient. Further, the presence of antibodies directed toward peptide K may be used to identify falsely positive Western blots for HIV virus.

In additional embodiments, the present invention provides for assay systems that may be used in the development of antiretroviral pharmaceuticals, as well as for model systems for various diseases, including autoimmune diseases and AIDS.

Furthermore, according to the invention, patients suffering from disease who have been found to exhibit the novel retrovirus of the invention or anti-retroviral antibodies may be treated with agents known to be useful in the treatment of retroviral diseases, including but not limited to, agents which interfere with reverse transcriptase function, such as, for example, nucleoside analogues (e.g. zidovudine or dideoxyinosine) and antisense oligonucleotides.

4. DESCRIPTION OF THE FIGURES

FIG. 1 (Panels A–H). Electron micrographs of intracisternal A-type retrovirus particles in RH9 cells exposed to salivary gland extracts from SS patients. RH9/MSC cells which were positive for reactivity to HIV-related antigens by antigen capture EIA were fixed, embedded and examined by electron microscopy. Panel A: Low power micrograph of RH9/MSC cells showing area of vacuolar concentration and the presence of a particle with the morphology of a typical intracisternal A-type retrovirus (arrow). Budding particles were not observed at the plasma membrane. Panel B: Selected area from another cell demonstrating HIAP at various stages of assembly. Panel C: Higher power micrograph of a budding HIAP (arrow). Panel D: Higher power micrograph of the HIAP in panel A (arrow). Panel E: Lower power micrograph of RH9 cells persistently-infected with the LA1 strain of HIV-1 prepared by same procedures as HIAP-infected cells. Arrows point to a few of the many particles with the morphology of typical lentiviruses at various stages of budding from the plasma membrane. Particles were not observed in cytoplasmic vacuoles. Panel F: Higher power micrograph of a budding HIV-1 particle showing core structure (arrow). Panel G: Higher power micrograph of the immature HIV virion shown at the largest arrow in panel E (arrow). Panel H: HIV-1 virions at various stages of post-budding maturation. Arrow points to mature HIV-1 virion with typical cylindrical core.

FIG. 2 (Panel A and B). RH9 cells exposed to salivary gland extracts produce particles antigenically-related to HIV with the hydrodynamic properties of an intracisternal A-type particle. Cell lysates from RH9/MSC cells were subjected to procedures previously used for purification of IAP from other species (Yang and Wivel, 1973, J. Virol. 11:287–298) as described in the text. Fractions from the 33 to 68% linear sucrose gradient were tested for the presence of reverse transcriptase activity using $Mn^{++}$ or $Mg^{++}$ as divalent cation, and for the presence of HIV-related antigens by an antigen-capture EIA. Aliquots from each fraction were also tested for refractive index to determine density. A control preparation also subjected to isopycnic banding consisted of concentrated supernatants from RH9 cells persistently-infected with HIV-1 (strain LA1 formerly designated HITI). Other controls are described in the text. Panel A: Gradient centrifugation of HIV-1$_{LA1}$. Panel B: Gradient centrifugation of HIAP. 0—0 Reverse transcriptase activity using Mg$^{++}$ as divalent cation; □—□ reverse transcriptase activity using Mn$^{++}$ as divalent cation; ▲—▲ HIV antigen determined by antigen capture EIA (Abbott).

FIG. 3 (Panels A-C). Divalent cation preference of the exogenous reverse transcriptase activities of HIAP, HIV and the polymerase found in uninfected RH9 cells. Standard reverse transcriptase reaction mixtures using polyrA:oligodT as template and primer containing the indicated amount of divalent cation were incubated for 60 minutes and the amount of label from [$^3$H]TTP which became acid precipitable was determined by scintillation counting. White bars represent incorporation using Mg$^{++}$ as divalent cation. Cross-hatched bars represent incorporation using Mn$^{++}$ as divalent cation.

FIG. 4. Template specificities of the HIAP-associated reverse transcriptase. Standard reaction mixtures using various template and primer combinations as indicated were performed in reaction mixtures containing 0.1 mM Mn$^{++}$. The amount of label from [$^3$H]TTP which became acid precipitable (and therefore was incorporated into retroviral nucleic acid) after 60 minutes was determined by scintillation counting.

5. DETAILED DESCRIPTION OF THE INVENTION

For purposes of clarity of disclosure, and not by way of limitation, the detailed description of the invention is divided into the following subsections:
(i) methods of culturing and isolating the autoimmune disease-associated retrovirus;
(ii) methods of diagnosis;
(iii) methods of treatment;
(iv) model systems for autoimmune disease; and
(v) assay systems of the invention.

5.1. METHODS OF CULTURING AND ISOLATING THE AUTOIMMUNE DISEASE-ASSOCIATED RETROVIRUS

According to the invention, the novel retrovirus described herein may be obtained by culturing lymphoid cells with cells or cell extracts obtained from patients suffering from an autoimmune disease such as systemic lupus Erythematosus, scleroderma, juvenile rheumatoid arthritis, or, preferably, from Sjogren's syndrome. Preferably, patient tissues are obtained from areas clinically involved, such as salivary or lacrimal gland from a Sjogren's syndrome patient. In a preferred embodiment of the invention, lip tissue from a Sjogren's syndrome patient may be obtained, homogenized (e.g. in a loose fitting tissue grinder in RPMI 1640 medium), and then added to a culture of lymphoid cells, preferably of T lymphocyte lineage. In a specific embodiment of the invention 0.5 g of such tissue is homogenized to yield 5 +ml of tissue extract, then added to cultures containing 10$^7$ cells of the RH9 subclone of HuT 78, a T-lymphoblastic cell line.

Once extracts have been added to the cell cultures, the cell cultures may then be examined from time to time for the presence of retrovirus or retroviral antigen, using standard virological techniques.

For example, cell supernatants or lysates of the cell cultures may be examined by electron microscopy for viral particles. Alternatively, supernatants and lysates may either be evaluated by enzyme linked immunoabsorbent assay (ELISA) techniques utilizing antibody reactive with retrovirus, for example, antibody reactive with HIV (including, but not limited to, antibodies reactive with the p24 protein) or may be screened using retrovirus-specific nucleic acid probes in order to identify retroviral nucleic acid. If retrovirus is present in the cultures, cultures may be expected to screen positive about six to twelve weeks after addition of extracts to cell cultures, although a longer culture period may, in some cases, be necessary. Of note, if cultures are analyzed by electron microscopy, retroviral particles of the invention may be expected to resemble intracisternal A-type particles (see, for example, Wivel and Smith, 1971, Int. J. Cancer 7:167-175).

Once evidence of the presence of retrovirus in culture has been obtained, virus may be further characterized using methods known in the art to determine its size, molecular biology, etc. For example, and not by way of limitation, cells containing virus may be disrupted in hypotonic buffer, and a microsomal fraction may be prepared. This preparation may then be made about 0.1% in Triton X-100, and then layered over a 48% sucrose cushion. Material which pellets through the cushion may then be applied over a 33-68% (w/v) sucrose gradient and then may be centrifuged at 100,000 g for about 12 hours. Fractions from the sucrose gradient may then be assayed for the presence of retroviral related antigens. The retroviral particles of the invention may be detected in the gradient at a density of about 1.22 g/cm$^3$ or in the range of 1.2 to 1.4 g/cm$^3$. In this manner, a substantially pure preparation of the retrovirus of the invention, henceforth referred to as HIAP (for human intracisternal A-type particle), may be produced.

Furthermore, it may be desirable to ascertain the characteristics of the reverse transcriptase comprised within HIAP. Detergent-disrupted preparations of HIAP may be tested for the ability to synthesize DNA at various concentrations of Mg$^{++}$ and Mn$^{++}$ using polyrA as a synthetic template and oligo dT as primer. According to the invention, the reverse transcriptase of HIAP may be expected to respond more favorably to Mn$^{++}$ rather than Mg$^{++}$, thereby distinguishing it from the reverse transcriptase of HIV, which "prefers"Mg$^{++}$ to Mn$^{++}$.

5.2. METHODS OF DIAGNOSIS

According to the invention, an HIAP-associated disease may be diagnosed in a patient by testing a sample from the patient for the presence of HIAP, HIAP nucleic acids or proteins, or anti-HIAP antibodies in which the presence of such particles, nucleic acids, proteins, or antibodies correlates positively with the presence of disease.

For example, a patient that presents with symptoms and signs consistent with diseases that have been characterized as autoimmune diseases, including systemic lupus erythematosus, scleroderma, juvenile rheumatoid arthritis, or Sjogren's Syndrome, or a non-autoimmune disease, such as amyotrophic lateral sclerosis, may be tested initially for the presence of anti-retrovirus antibodies, including, but not limited to, antibodies reactive with HIV antigens such as p24.

In preferred diagnostic methods of the invention, antibodies that recognize a 45,000 dalton, 61,000 dalton, and/or 70,000 dalton protein of HIAP may be detected and/or measured. As exemplified in Section 7, infra, about 90 percent of autoimmune disease patients tested (including patients suffering from systemic lupus erythematosus, scleroderma, Sjogren's Syndrome, and juvenile rheumatoid arthritis) produced antibodies toward these proteins. In most preferred, but non-limiting, embodiments of the invention, detection and/or measurement of levels of such antibodies may be used to diagnose systemic lupus erythematosus (SLE), scleroderma, juvenile rheumatoid arthritis (JRA), amyotrophic lateral sclerosis (ALS), or Sjogren's Syndrome (SS), but the diagnostic methods of the present invention are not limited to these conditions. However, the presence of such antibodies appears not to be supportive of a diagnosis of adult rheumatoid arthritis or polymyositis. In order to support a diagnosis of autoimmune disease, the level of antibody directed toward the 45,000 dalton viral protein (p45), the 61,000 dalton viral protein (p61), and/or the 70,000 dalton viral protein (p70), may preferably but not by way of limitation, be at least about three times the level of such antibody detected in a patient who is not suffering from an autoimmune disease or from HIV infection.

The present invention further provides for methods of diagnosing a retroviral infection and/or an autoimmune disease in a patient comprising detecting the presence of antibodies directed toward peptide (Peptide A [SEQ. ID NO: 1]); (Peptide D [SEQ. ID NO: 2]); (Peptide E [SEQ. ID NO: 3]); (Peptide G [SEQ. ID NO: 4]); (Peptide H [SEQ. ID NO: 5]); (Peptide I [SEQ. ID NO: 6]); (Peptide J [SEQ. ID NO: 7]); (Peptide K [SEQ. ID NO: 8];) fragments or derivatives of retroviral gag proteins, in a patient sample, in which the presence of such antibodies correlates positively with retroviral infection and/or autoimmune disease. In particular embodiments, the presence of antibodies toward the following peptides may be detected:

Peptide A PIVQNIQGQMVHQAIS
Peptide D SEGATPQDLNTMLNTVG
Peptide E GHQAAMQMLKETINEE
Peptide G IRQGPKEPFYKTLRAEQAS
Peptide H KTLRAEQASQEVKNWMTET
Peptide I ETLLVQNANPDCKTILKAL
Peptide J KALGPAATLEEMMTACQ
Peptide K MMTACQGVGGPGHKA According to the invention, the presence of antibodies directed toward peptides D, E, G, H, I, or K correlates positively with HIAP retroviral infection and/or autoimmune disease, and the presence of antibodies directed toward peptide K is strongly suggestive of a diagnosis of autoimmune disease rather than HIV infection. Thus, the detection of antibodies directed toward peptide K diminishes the risk of a false positive diagnosis of HIV infection. The present invention therefore provides for a method of diminishing the risk of a false positive diagnosis of HIV infection, comprising testing a patient who has been found to express anti-HIV antibodies for the presence of antibodies that bind to peptide K, in which the presence of antibodies that bind to peptide K suggests that the patient may not be infected with HIV. Of course, it is possible that a patient may be infected with both HIV and HIAP, in which case the patient may express antibodies toward both HIV and HIAP.

Antibody detection may be performed utilizing any standard technique, including ELISA or Western Blot techniques, in which a sample from a patient may be tested for the presence of anti-retroviral antibodies by exposing the serum to immobilized retrovirus or retroviral antigen, and then detecting antibody that has bound to immobilized virus or viral antigen (e.g. by binding of a second labeled antibody capable of reacting with the antibody adherent to virus or antigen).

For example, and not by way of limitation, proteins from HIAP may be subjected to Western blot analysis.

In a specific, nonlimiting embodiment of the invention, Western blotting may be performed as follows: HIAP producing RH9/MSC cells may be prepared as described in Section 6.1, infra, disrupted in a hypotonic buffer, and used to prepare a microsomal fraction, e.g., by disruption in 0.1 percent Triton X-100, and layering of lysate over a 48 percent sucrose cushion followed by centrifugation for one hour at 100,000 g. The pelleted material may then be collected, applied over a 33–68 percent (weight/volume) sucrose gradient, and centrifuged at 100,000 g for about 12 hours. Individual fractions of the gradient may then be loaded into individual wells of a sodium dodecyl sulfatepolyacrylamide slab gel of about a 7–15 percent polyacrylamide gradient and the proteins in each fraction may be electrophoretically separated, e.g. by electrophoresis at 24 amps (constant current) for about three hours. The resolved proteins in the slab gel may then be transferred to a sheet of nitrocellulose (e.g. by electroblotting using a Transblot (Biorad) apparatus) and then reacted with a reference serum, e.g. from a person suffering from scleroderma, SS, SLE or JRA. Antibodies bound to the nitrocellulose sheets may be detected by reacting the sheets sequentially with biotinylated goat anti-human immunoglobulin, avidin coupled to horse radish peroxidase, and nitroblue tetrazolium substrate. Fractions of the gel containing proteins with reactivity to autoimmune patient serum and which also correspond to a peak in HIAP-specific reverse transcriptive activity (see Section 6.1, infra), may be pooled and loaded into a single wide well in a second sodium dodecyl sulfate 7–15 percent polyacrylamide gradient gel and subjected to electrophoresis at about 24 amps for three hours. The resolved proteins in the slab gel may then be electroblotted to a sheet of nitrocellulose which may then be reacted with sera from persons suspected of suffering from HIAP-mediated disease. Binding of antibodies may be detected as described supra, or by other standard methods.

Alternatively, substantially pure preparations of p45, p61, and/or p70 proteins may be used as binding antigen(s) in standard ELISA type assays. These proteins may be prepared, for example, from lysates of HIAP producing cultures by sodium dodecyl sulfate polyacrylamide gel electrophoresis followed by elution of the appropriate protein band(s). Such proteins, or antigenic portions thereof, may also be produced by chemical synthesis or recombinant DNA technology.

Further, according to the invention, tissue biopsies, preferably from clinically involved areas, may be tested for the presence of retrovirus or retroviral antigens by in situ binding of anti-retroviral antibody to tissue sections or cells using standard techniques.

In additional embodiments of the invention, the presence of retrovirus may be detected by culturing cells from a patient in the presence of cell extracts made from the patient's cells or tissues, and then detecting the presence of HIAP in culture according to the methods set forth in Section 5.1. In one specific embodiment of the invention, cells may be scraped from the buccal mucosa of a patient who is suspected of suffering from Sjogren's syndrome and then tested for the presence of virus.

A sample from a patient may preferably be a serum sample, but may also be a sample of any body tissue or fluid, including, but not limited to skin, liver, blood, saliva, urine, cerebrospinal fluid, joint fluid, semen, nasal secretions, etc.

The present invention also provides for a method of diagnosing a HIAP-associated disease in a patient comprising detecting HIAP nucleic acids in a sample from the patient, in which the presence of HIAP nucleic acid correlates positively with a diagnosis of the disease. Diseases which may be diagnosed according to this method include, but are not limited to, SLE, scleroderma, JRA, SS, or ALS. In particular, nonlimiting embodiments of the invention, retroviral nucleic acids may be detected by hybridization techniques utilizing, as a probe, detectably labeled nucleic acid that comprises sequence that encodes a peptide having an amino acid sequence substantially identical to the sequence of Peptide A, Peptide D, Peptide E, Peptide G, Peptide H, Peptide I, Peptide J, or preferably Peptide K (supra). The nucleic acid probe may be ribonucleic acid or deoxyribonucleic acid, and may be labeled with a radioactive isotope, biotin, or any other detectable compound. The hybridization techniques may utilize RNA or DNA prepared from a patient sample (e.g. using Northern blot, Southern blot, or dot blot methods) or may utilize a tissue or cell sample from the patient (e.g. using in situ hybridization methods).

In further embodiments of the invention the presence of retrovirus or anti-retroviral antibodies may be useful in determining the clinical progression of disease, in which case a decline in retrovirus may indicate remission of the disease and/or a positive response to treatment.

5.3. METHODS OF TREATMENT

The present invention provides for methods of treating HIAP-associated diseases comprising administering to a patient in need of such treatment an effective amount of a compound that is effective in the treatment of retroviral disease, such as an anti-retroviral therapy. In preferred embodiments of the invention, the HIAP-associated disease has been categorized as an autoimmune disease. In most autoimmune diseases, the mainstay of therapy has been immunosuppressive treatment. The association between a retrovirus and autoimmune disease presents the possibility that anti-retroviral therapy may be effective in treating some or all patients with the disease. Because it remains unclear whether the presence of retrovirus defines a subgroup of autoimmune disease patients, it is recommended that anti-retroviral medication be administered only to those patients with evidence of retroviral infection.

Anti-retroviral therapies include but are not limited to administration of an effective amount of a compound or compounds which interfere with the function of reverse transcriptase, including nucleoside derivatives such as zidovudine, dideoxyinosine, dideoxydidehydrothymidine, etc.

The present invention further provides for methods of treatment of an HIAP-associated disease, e.g. an autoimmune disease, comprising administering an effective amount of antisense oligonucleotide that interferes with the transcription or translation of a human retroviral gene to a patient in need of such treatment. Such oligonucleotide may, in particular, nonlimiting embodiments of the invention, encode a peptide having an amino acid sequence substantially identical to the sequence of Peptide A, Peptide D, Peptide E, Peptide G, Peptide H, Peptide I, Peptide J, or Peptide K, and may be comprised in a larger nucleic acid molecule. Such oligonucleotides may be ribonucleic acid or deoxyribonucleic acid, and may or may not comprise phosphorothioate linkages.

In additional embodiments, antibody directed toward HIAP, or a component thereof, that is polyclonal antibody or monoclonal antibody, may be administered as treatment to a patient suffering from an autoimmune disease. Such antibodies may not substantially bind to uninfected human cells or tissue, i.e. they may not be substantially similar to autoimmune antibodies.

In preferred embodiments the present invention provides for the treatment of systemic lupus erythematosus, Sjorgren's Syndrome, juvenile rheumatoid arthritis, and scleroderma by anti-retroviral therapy.

5.4. MODEL SYSTEMS FOR THE STUDY OF DISEASE

The substantially purified retrovirus, HIAP, of the invention may be used to generate model systems for various diseases including, but not limited to, autoimmune diseases and AIDS. For example, antibodies directed toward the HIAP retrovirus may be induced in laboratory animals which may subsequently be evaluated for autoimmune phenomena. For example, and not by way of limitation, retrovirus containing cells generated according to the methods set forth in Section 5.1 may be administered, together with adjuvant, to a primate; standard "booster" doses may subsequently be administered. Animals may then be followed clinically for the appearance of symptoms and signs of autoimmune disease, including the sicca syndrome; tissue biopsies may also be studied.

An important feature of the present invention is that it appears that the retrovirus of the invention is related to HIV, but differs in its cytopathicity. The retrovirus of the invention may provide a method for studying the immunological aberrations caused by HIV which are not due to direct cytopathic effects. Further, inactive formulations of the retrovirus of the invention, or antigenic portions thereof, may be useful in the generation of an anti-autoimmune disease, and, possibly, an anti-HIV vaccine.

5.5. ASSAY SYSTEMS OF THE INVENTION

The present invention also provides for assay systems that may be used to evaluate the efficacy of compounds toward altering the effects of HIAP infection and treating HIAP-associated disease. In such assay systems, cells, tissue or whole organisms that express HIAP may be exposed to a test agent and then evaluated to determine the effects of the test agent on the cells, tissue culture, or organism. Alternatively, cells, tissue, or whole organisms may be exposed to HIAP that has been exposed to test agent.

Cells that may be utilized in such an assay include, but are not limited to, lymphoid cells, preferably T cell lines, and reticuloendothelial cells, such as macrophage cell lines.

Tissues that may be utilized include any tissue that comprises cells that are capable of expressing HIAP, such as bone marrow, spleen, salivary or lacrimal gland tissue, peripheral blood mononuclear cells, dendritic cells, synovial cells, etc.

Organisms that may be utilized include single cell or multicellular organisms such as bacteria, yeast, protozoa, nematodes, insects, birds, amphibia, reptiles, or mammals.

The cells, tissue, or organism may then be exposed to an infective concentration of HIAP which has been purified or which is not purified but, for example, is in the form of a cell lysate, in order to produce a culture of cells or a tissue or an organism that expresses HIAP, referred to hereafter as an HIAP assay system. For example, a T lymphocyte HIAP assay system may be prepared by adding homogenized lip tissue from a Sjorgren's patient to a culture of T lymphocytes, as described in Section 5.1, supra.

Test agent may then be added to the HIAP assay system. Preferably, a number of HIAP assay systems may be prepared in parallel and simultaneously be administered varying concentrations of test agent. An untreated or sham treated HIAP assay system may preferably be used as a control.

Suitable test agents include any compound or combination of compounds which might be suspected of exerting either anti-HIAP activity or activity that limits secondary effects of HIAP expression. For example, compounds that interfere with the function of reverse transcriptase may be used, including but not limited to zidovudine, dideoxyinosine, dideoxydidehydrothymidine, etc. As further examples, antisense oligonucleotides, antibodies, or compounds that have been used to treat autoimmune disease, including immunosuppressive agents such as corticosteroids, imuran, etc. may be evaluated for their effects in the HIAP assay system. The present invention accordingly provides for assay systems that may be used in the rational design of compounds that may inhibit any step of viral infection, or any viral component, such as HIAP reverse transcriptase or protease.

Parameters that may be measured include any primary or secondary effects of HIAP expression, including number of intracisternal A particles, amount of reverse transcriptase activity, amount of viral protein (e.g. p45, p61 and/or p70) expressed, level of immune system activation, viral protease activity, lymphokine/cytokine production, cell viability, mitotic activity, spread of HIAP infection, cytopathic effects, the level of viral RNA or proviral DNA, etc. In whole organisms such as laboratory animals, physiological effects including anatomical/histological changes, behavioral changes, alteration in metabolism, renal function, etc., may be measured.

A diminution of an effect of HIAP expression resulting from administration of test agent, relative to the comparable effect of HIAP expression measured in an untreated HIAP assay system indicates that the test agent may be useful in the treatment of HIAP-mediated disease.

6. EXAMPLE: SJOGREN'S SYNDROME: INITIAL CHARACTERIZATION OF A HIV-RELATED INTRACISTERNAL A-TYPE RETROVIRAL PARTICLE PRESENT IN LYMPHOBLASTOID CELLS EXPOSED TO SALIVARY GLAND HOMOGENATES

Sjogren's Syndrome (SS) is diagnosed clinically by histologic examination of the salivary gland for lymphocytic infiltration. Lip tissue contains salivary glands and is the anatomic location of choice for biopsy. An infectious agent was cultured from salivary gland tissue of an SS patient. Salivary gland tissues were collected by lip biopsy of six persons with SS. The tissues were then frozen on dry ice and stored at $-70°$ C.

Approximately 0.5 g of tissue was homogenized in a loose-fitting tissue grinder in 5 ml RPMI 1640 medium. Then 0.5 ml of the crude tissue homogenate was added to cultures containing 107 cells of the RH9 subclone of HuT 78, a T-lymphoblastic cell line.

Since a portion of SS patients made antibodies reactive with the gag proteins of HIV we postulated that antibodies reactive to HIV gag proteins might react with a retrovirus of SS patients. Therefore, cell-free supernatants and cell lysates were screened in a sensitive and specific antigen capture enzyme-linked immunoassay (Abbott). Uninfected RH9 cells did not produce HIV antigens in cell supernatants or cell lysates detectable in this assay. After 6 weeks, lysates of the cells exposed to one salivary gland biopsy (RH9/MSC) became positive for p24 antigen by an antigen capture EIA (Table I).

TABLE I

Production of HIV-related antigen by RH9 cultures exposed to SS extracts

| Patient | Diagnosis | Time post-exposure (weeks) | | | | | | |
|---|---|---|---|---|---|---|---|---|
| | | 2 | 4 | 6 | 8 | 10 | 12 | 16 |
| MSC | SS | − | − | + | + | + | + | + |
| HD | SS | − | − | − | − | − | + | + |
| DH | SS | − | − | − | − | − | − | − |
| CR | SS | − | − | − | − | − | − | − |
| JS | SS | − | − | − | − | − | − | − |
| FS | SS | − | − | − | − | − | − | − |
| DC | normal | − | − | − | − | − | − | − |

However, cell-free supernatants from RH9/MSC cells did not contain significant levels of HIV-related antigens. Lysates of cells exposed to a second biopsy (RH9/HD) became positive for expression of p24 reactivity after 10 weeks in culture. Cultures from four other biopsies from SS patients and one healthy individual remained negative for HIV reactive antigens by EIA for 24 weeks.

Figure 1:
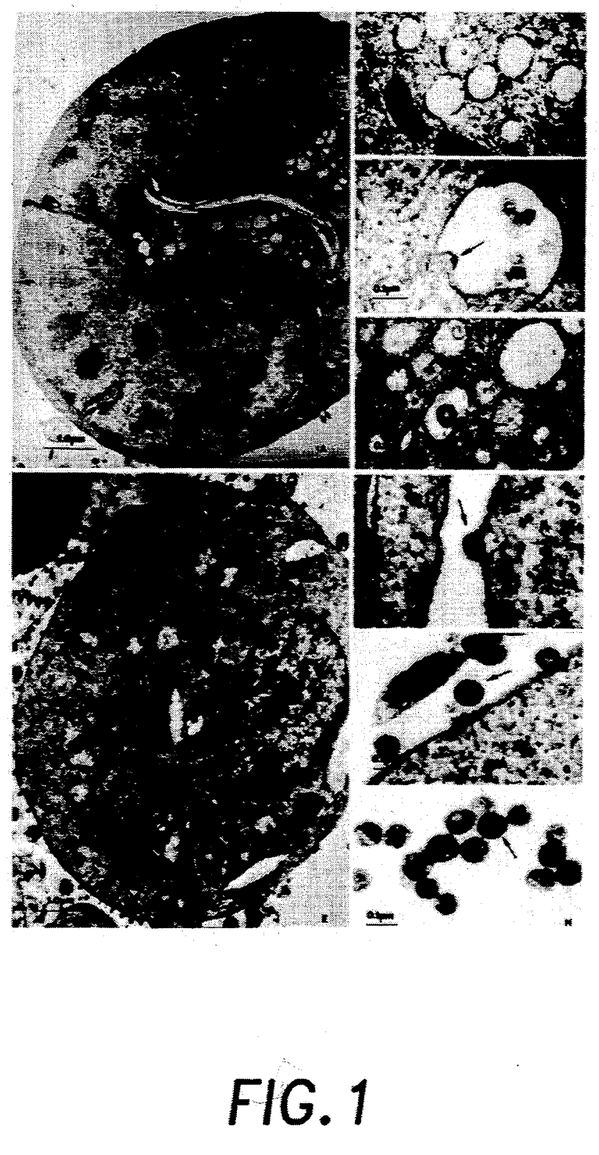

To determine if expression of the HIV antigenic reactivity of cells exposed to SS patient salivary gland homogenates was due to production of a viral particle the cells were examined by transmission electron microscopy. HIV, a lentivirus, matures principally at the plasma membrane of infected T-lymphoblastoid cells (Gelderblom et al., 1989, Arch. Virol. 106:1–3, FIG. 1, panels C–H). Despite the fact that the cells were reactive to anti-HIV antibodies, the RH9/MSC cells failed to produce particles which matured at the plasma membrane. However, evident in some cells in this culture were particles contained within intracytoplasmic vacuoles (FIG. 1, panels A–D). These results are consistent with the absence of HIV-related antigen in culture supernatants. The intracisternal particles consisted of two electron dense concentric rings giving a "doughnut-shaped" appearance. Particles with this distinctive morphology were not found in uninfected RH9 cells or in RH9 cells infected with HIV despite an extensive search. The particles are morphologically similar to intracisternal A-type particles which have been described in a variety of normal and transformed cells from other species (Wivel and Smith, 1971, Int. J. Cancer 7:167–175.; Calarco and Szollosi, 1973, Nature (New Biology) 243:91–93; Wivel et al., 1973, J. Virol.

11:329–334; Meitz et al., 1987, J. Virol. 61:3020–3029; Kuff and Lueders, 1988, Ad. Cancer Res. 52:184–276). For the purposes of this discussion we will refer to the structures as human intracisternal A-type particles (HIAP).

Figure 2A:
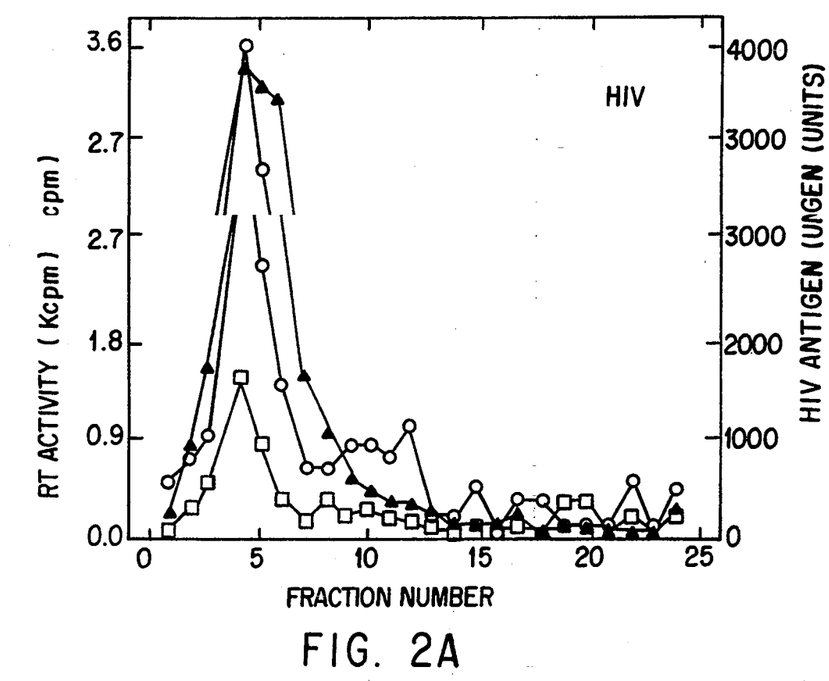
Figure 2B:
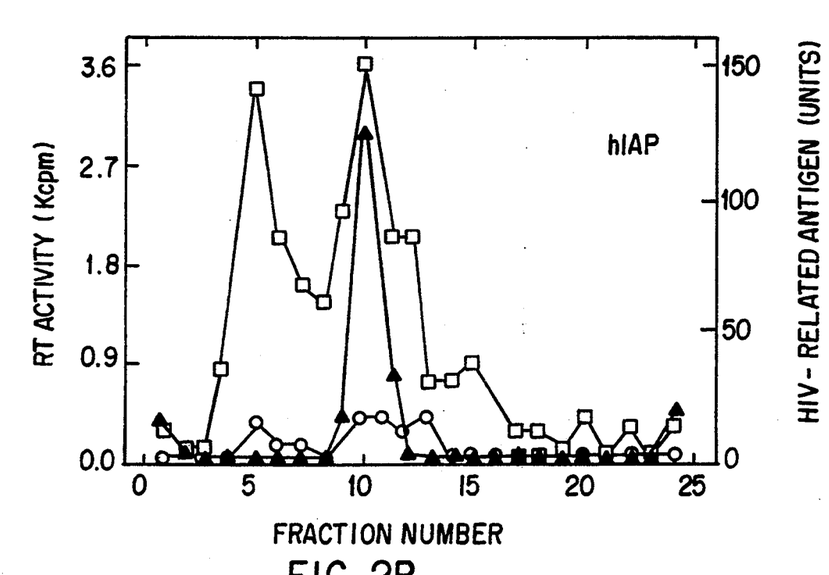

To physically characterize the particles produced by the RH9/MSC cells, we employed protocols developed for murine A-type retroviruses (Yang and Wivel, 1973, J. Virol. 11:287–298). Cells were disrupted in hypotonic buffer, and a microsomal fraction was prepared. This preparation was made 0.1% in Triton X-100 and layered over a 48% sucrose cushion. Material which pelleted through the cushion was then applied over a 33–68% (w/v) sucrose gradient and centrifuged at 100,000 ×g for 12 hours. Similar preparations were made from HIV/RH9 cells and uninfected RH9 cells. In addition, concentrated cell-free supernatants from RH9/MSC, RH9/HIV and uninfected RH9 cells were sedimented in parallel 33–68% sucrose gradients. Fractions of each of the gradients were assayed for the presence of HIV-related antigens by antigen-capture EIA. The major peak of HIV antigen (fractions 4–6) sedimented in this gradient at a density of 1.14–1.16 g/cm$^3$ consistent with previous determinations of the density of HIV (FIG. 2, panel A). This peak is broad because HIV tends to shed the major envelope protein, SU. Additional minor peaks in the gradient correspond to degraded virions or viral antigens associated with subcellular components. RH9/HIV infected cells contain HIV antigenic reactivity dispersed throughout the gradient. RH9/MSC cells did not produce significant levels of HIV-related antigen in the concentrated supernatant fluids, however, a peak of HIV-related antigen from the RH9/MSC cells was detected in the gradient at a density of approximately 1.22 g/cm$^3$ (FIG. 2, panel B, fraction 10). The cellular distribution of the antigenic reactivity is also consistent with the electron microscopic observations. Moreover, this density is similar to that previously determined for A-type particles from other species (Yang and Wivel, 1973, J. Virol. 11:287–298; Robertson et al., 1975, J. Virol. 15:407–415).

One defining characteristic of retroviruses, including A-type retroviruses, is the presence in the viral particle of an RNA-dependent DNA polymerase (reverse transcriptase, RT) (Wilson and Kuff, 1972, PNAS 69:1531–1536; Wong-Staal et al., 1975, J. Virol. 16:887–896; Robertson et al., 1975, J. Virol. 15:407–415). Reverse transcriptases of various retroviruses can often be distinguished on the basis of substrate or ionic preferences (Waite and Allen, 1975, J. Virol. 16:872–879). For example, HIV prefers $Mg^{++}$ over $Mn^{++}$ as a divalent cation when using poly rA as a template and oligo dT as a primer, whereas the reverse preference is shown by the RT of HTLV-I (Rho et al., 1981, Virology 112:355–360); Hoffman et al., 1985, Virology 147:326–335).

Figure 3A:
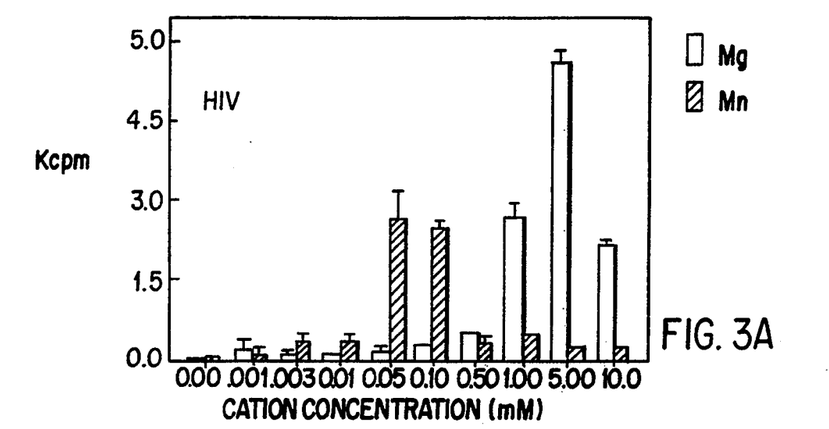
Figure 3B:
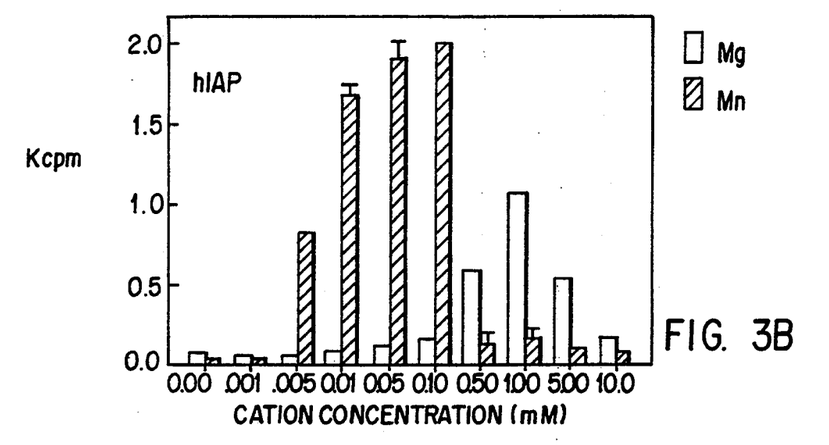

To determine if the HIAP produced by the RH9/MSC cells contain a reverse transcriptase activity and to define possible distinguishing properties from HIV RT we compared the ability of detergent-disrupted preparations of these viruses to synthesize DNA at various concentrations of $Mg^{++}$ and $Mn^{++}$ using poly rA as a synthetic template and oligo dT as a primer. The optimum concentrations for HIV RT activity was 5 mM $Mg^{++}$, whereas the highest activity when $Mn^{++}$ was used was 0.05 mM (FIG. 3, panel A). Under these conditions, the optimum activity using $Mg^{++}$ as divalent cation was 2-fold higher than the highest activity using $Mn^{++}$ as divalent cation. Thus, HIV reverse transcriptase showed a definite preference for $Mg^{++}$ over $Mn^{++}$ as divalent cation in agreement with determinations by Hoffman et al. (1985, Virology 147:326–335). In contrast, the highest RT activities associated with HIAP preparations were obtained using $Mn^{++}$ as divalent cation (FIG. 3, panel B). 0.1 mM $Mn^{++}$ gave the highest activity which was nearly 2-fold higher than activity at the optimum $Mg^{++}$ concentration (1.0 mM). The results indicate that the RT of the HIAP preparation differs from that of HIV. Fractions of each of the sucrose gradients assayed for the presence of HIV-related antigens were also assayed for $Mg^{++}$- and $Mn^{++}$-dependent RT activities (FIG. 3). The peak of HIV-related antigen from RH9/MC (1.22 g/cm$^3$) corresponded to a major peak of the $Mn^{++}$-dependent RT activity (FIG. 3, panel B).

Figure 3C:
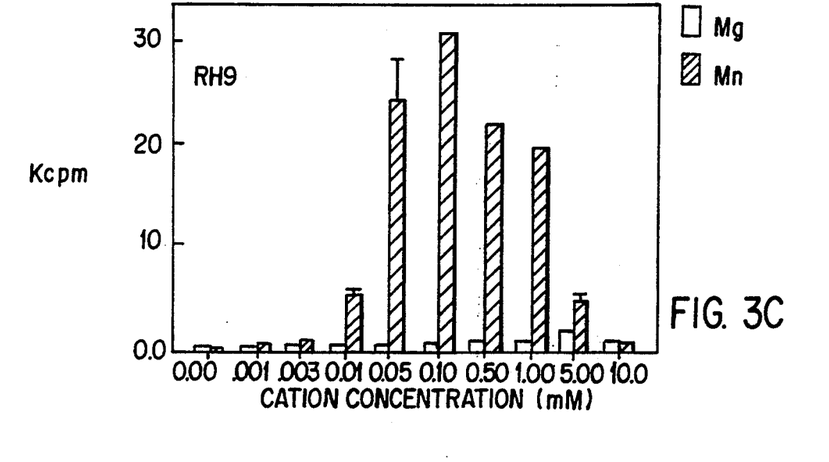

Uninfected RH9 cells did not contain HIV-related antigens detectable by this assay in either cell lysates or cell-free supernatants. These cells, however, did contain an endogenous RT activity as is commonly observed in uninfected (Nelson et al., 1978, Proc. Natl. Acad. Sci. U.S.A. 75:6263–6267; Sarngadharan et al., 1978, Biochem. Biophys. Acta 516:419–487) cells. This cellular RT could be distinguished from the HIAP-associated RT by sedimentation in a linear sucrose gradient (FIG. 3, panel B, fraction 5 versus fraction 10) and by a greater preference for $Mn^{++}$ over $Mg^{++}$ (over 20-fold compared to 2-fold, FIG. 3, panel C) as well as other cation- and template-preference characteristics.

Figure 4:
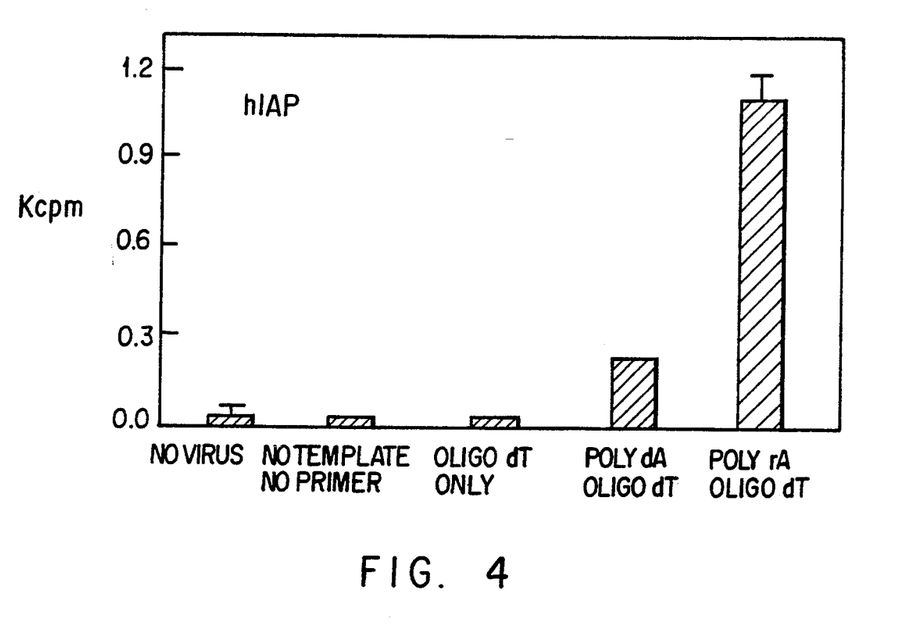

In additional studies we observed that the HIAP associated RT prefers to utilize RNA (poly rA) over DNA (poly dA) as template (FIG. 4). The HIAP preparation also could not effectively synthesize DNA in a reaction mixture containing only oligo dT. The results of these experiments indicate that the preparation does not contain sufficient levels of a DNA-dependent DNA polymerase nor a deoxyribonucleotidyl (terminal) transferase to account for the observed DNA polymerase activity (Harrison et al. 1976, Biochem. Biophys. Res. Comm. 69:63–67).

7. EXAMPLE: DETECTION OF ANTIBODIES DIRECTED TOWARD HIV AND HIV-RELATED INTRACISTERNAL A-TYPE RETROVIRAL PARTICLE IN PATIENTS WITH VARIOUS AUTOIMMUNE DISEASES

7.1. MATERIALS AND METHODS

7.1.1. WESTERN BLOTTING

RH9/MSC cells, which are infected with HIAP, were disrupted in a hypotonic buffer, and a microsomal fraction was prepared. This was made 0.1% in Triton X100 and layered over a 48% sucrose cushion. Material which pelleted through the cushion was then applied over a 33–68% (w/v) sucrose gradient and centrifuged at 100,000 ×g for 12 hours. Individual fractions (fractions 2–19) of the gradient were loaded into individual wells of a SDS PAGE slab gel apparatus and the proteins in each fraction were electrophoretically separated. The resolved proteins in the slab gel were then transferred (electroblotted) to a sheet of nitrocellulose which was then reacted with a reference serum from a person with either Sjogren's Syndrome or SLE. Antibodies bound to the nitrocellulose sheets were detected by reacting the sheets sequentially with biotinylated goat anti-human immunoglobulin, avidin coupled to horse radish peroxidase and nitroblue tetrazolium substrate. Fractions of the gel containing proteins with reactivity to autoimmune patient sera and which also corresponded to the peak of HIAP-specific reverse transcriptase were pooled and loaded into single wide well of a SDS-PAGE slab gel apparatus. The resolved proteins in the slab gel were then transferred (electroblotted) to a sheet of nitrocellulose which was then reacted with sera from persons with various autoimmune diseases. Antibodies bound to the nitrocellulose sheets were detected by Western blotting.

Serological data relating to the presence of p24 and p17 reactive antibodies was obtained as described in Talal et al., 1990, Arthritis and Rheumatism 33: 774–781 and Talal et al., 1990, J. Clin, Invest. 85: 1866–1871.

7.1.2. ELISA

Synthetic peptides having the sequences for peptides A-K as presented in Section 5.2, supra, were prepared on a Biosearch Peptide Synthesizer by standard t-Boc chemistry and cleaved from the supporting resins using hydrogen fluoride. Peptides were purified by G-25 column chromatography and were at least 95% pure as determined by analytical reverse phase high performance liquid chromatography (HPLC) on a C18 column. ELISA assays were performed according to the following methods. 1 µg of the synthetic peptides in 100 µl of 0.1M bicarbonate buffer (pH 9.6) were bound to individual wells of polystyrene microtiter plates (Immulon) and incubated overnight at 37° C. The wells were washed three times in buffered saline containing 0.05% Tween 20 and reacted with dilutions of sera (1:100 to 1:100,000) from healthy normal persons or persons with various autoimmune diseases or AIDS. Antibodies specifically bound to ELISA plates were detected by reacting the wells sequentially with biotinylated-goat anti-human immunoglobulin (1:1000 dilution), avidin coupled to horse radish peroxidase and 0-nitrophenyl substrate. After color development of the substrate, the optical density of each well was read in a ELISA reader at 405 nm.

7.2. RESULTS

7.2.1. REACTIVITY OF AUTOIMMUNE DISEASE PATIENT SERA WITH HIV PROTEINS

As shown in Table II, sera from patients suffering from a variety of autoimmune diseases have also been found to be reactive with p24 and/or p17 gag proteins on standard HIV Western blot assays, indicating that a number of autoimmune diseases may be associated with the novel HIAP retrovirus of the present invention. Autoimmune diseases which appear to be most strongly correlated with the production of anti-retroviral antibodies include systemic lupus erythematosus, juvenile rheumatoid arthritis, and scleroderma. There was much less of a correlation with adult rheumatoid arthritis and polymyositis.

TABLE II

Antibodies in autoimmune patient sera positive for reactivity to p24 and/or p17 HIV proteins

| Diagnosis | number tested[a] | Percent Positive |
|---|---|---|
| Sjogren's Syndrome | 14/47 | 29.8 |
| Systemic lupus erythematosus | 22/61 | 36.1 |
| Scleroderma | 16/55 | 29.1 |
| Juvenile Rheumatoid Arthritis | 7/31 | 22.5 |
| Adult Rheumatoid Arthritis | 3/59 | 5.1 |
| Polymyositis | 1/65 | 1.5 |

TABLE II-continued

Antibodies in autoimmune patient sera positive for reactivity to p24 and/or p17 HIV proteins

| Diagnosis | number tested[a] | Percent Positive |
|---|---|---|
| Autoimmune diabetes | 0/20 | 0.0 |
| Hansen's Disease | 0/12 | 0.0 |
| "Normal" Donors | 6/175 | 3.4 |

[a]Sera were positive to p24 and/or p17 gag proteins on standard HIV western blot (Biotech/Dupont).

7.2.2. REACTIVITY OF AUTOIMMUNE DISEASE PATIENT SERA WITH HIAP PROTEINS

Antibodies in the sera of 90% of the 60 autoimmune patients tested, including patients suffering from systemic lupus erythematosus, Sjogren's Syndrome, or juvenile rheumatoid arthritis, specifically interacted by Western blotting with three HIAP proteins of $M_r$ 45,000 (p45), 61,000 (p61) and 70,000 (p70) (Table III). A rabbit antiserum to p24 also reacted strongly to the p61 and p70 proteins indicating that these proteins from HIAP-producing cells contained epitopes in common with HIV CA protein. These proteins were not present in Western blots prepared from uninfected H9 cells indicating that these were specific for the HIAP. Furthermore, only one of 45 sera from normal donors reacted with any of these three proteins, and this serum gave an indeterminate Western blot against HIV p24. Our results indicate that reactivity to HIAP proteins is a broad and specific marker for various systemic diseases.

TABLE III

Antibodies in autoimmune patient sera positive for reactivity to HIAP proteins

| Diagnosis | Reactive Sera number tested | Percent positive |
|---|---|---|
| Systemic lupus erythematosus | 22/24 | 91.7 |
| Sjogren's Syndrome | 15/17 | 88.2 |
| Juvenile Rheumatoid Arthritis | 18/19 | 94.7 |
| Total Autoimmune Patients | 54/60 | 90.0 |
| Normal Controls | 1/45 | 2.2 |

7.2.3. ELISA ASSAYS

In addition, we have performed specific ELISA-based assays using synthetic peptides with linear sequences derived from retroviral gag proteins. Synthetic peptides A-K (see Section 5.2, supra) were bound to polystyrene plates and reacted with sera from persons with various autoimmune diseases, AIDS and normal sera. Antibodies bound to ELISA plates were detected by reacting the sheets sequentially with biotinylated goat anti-human immunoglobulin, avidin coupled to horse radish peroxidase and 0-nitrophenyl substrate. These epitope mapping studies identified linear retroviral epitopes recognized by antibodies in both autoimmune and AIDS patient sera (e.g. peptides D, E, G, H). We also identified an epitope(s) recognized by most autoimmune patient sera, but not sera from HIV patients (peptide K) and epitopes recognized only by indeterminants on Western blots (peptides A, J).

Various publications are cited herein, the disclosures of which are incorporated by reference in their entireties.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

---

What is claimed:

1. A method of supporting a diagnosis of systemic lupus erythematosus in a patient, comprising testing a sample from the patient for the presence of antibodies directed toward a human intracisternal A-type retroviral particle, having the ATCC accession number VR 2394, which exhibits a density of about 1.2 on a 33–68% sucrose gradient and which comprises a reverse transcriptase that exhibits greater activity in a solution comprising 0.10 mM manganese ions than in a solution comprising 0.10 mM magnesium ions, by determining the ability of antibodies in the patient sample to bind to the human intracisternal A-type retroviral particle, in which the presence of such antibodies correlates positively with the diagnosis of systemic lupus erythematosus.

2. A method of supporting a diagnosis of systemic lupus erythematosus in a patient, comprising measuring the level of antibodies that bind to a human intracisternal A-type retroviral particle, having the ATCC accession number VR 2394, which exhibits a density of about 1.2 on a 33–68% sucrose gradient and which comprises a reverse transcriptase that exhibits greater activity in a solution comprising 0.10 mM manganese ions than in a solution comprising 0.10 mM magnesium ions, in which an antibody level that is at least about three times greater than the antibody level of a person who is not suffering from the disease supports a diagnosis of systemic lupus erythematosus in the patient.

3. A method of supporting a diagnosis of systemic lupus erythematosus in a patient, comprising testing a sample from the patient for the presence of antibodies directed toward a peptide having the sequence MMTACQGVGGPGHKA (Sequence ID NO: 8), in which the presence of such antibodies supports the diagnosis of systemic lupus erythematosus.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:1:

Pro Ile Val Gln Asn Ile Gln Gly Gln Met Val His Gln Ala Ile Ser
   1               5                   10                  15

( 2 ) INFORMATION FOR SEQ ID NO:2:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:2:

Ser Glu Gly Ala Thr Pro Gln Asp Leu Asn Thr Met Leu Asn Thr Val
   1               5                   10                  15

Gly ( 2 ) INFORMATION FOR SEQ ID NO:3:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:3:

Gly His Gln Ala Ala Met Gln Met Leu Lys Glu Thr Ile Asn Glu Glu
   1               5                   10                  15

( 2 ) INFORMATION FOR SEQ ID NO:4:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:4:

Ile Arg Gln Gly Pro Lys Glu Pro Phe Tyr Lys Thr Leu Arg Ala Glu
   1               5                   10                  15

Gln Ala Ser ( 2 ) INFORMATION FOR SEQ ID NO:5:

( i ) SEQUENCE CHARACTERISTICS:
  ( A ) LENGTH: 19 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:5:

Lys Thr Leu Arg Ala Glu Gln Ala Ser Gln Glu Val Lys Asn Trp Met
1               5                   10                  15
Thr Glu Thr ( 2 ) INFORMATION FOR SEQ ID NO:6:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:6:

Glu Thr Leu Leu Val Gln Asn Ala Asn Pro Asp Cys Lys Thr Ile Leu
1               5                   10                  15
Lys Ala Leu ( 2 ) INFORMATION FOR SEQ ID NO:7:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:7:

Lys Ala Leu Gly Pro Ala Ala Thr Leu Glu Glu Met Met Thr Ala Cys
1               5                   10                  15
Gln ( 2 ) INFORMATION FOR SEQ ID NO:8:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:8:

Met Met Thr Ala Cys Gln Gly Val Gly Gly Pro Gly His Lys Ala
1               5                   10                  15